(12) United States Patent
Clark et al.

(10) Patent No.: US 6,268,439 B1
(45) Date of Patent: Jul. 31, 2001

(54) POLYOLEFIN-SUBSTITUTED DICARBOXYLIC DERIVATIVES

(75) Inventors: Michael Thomas Clark, Chester; Indu Sawhney; Hendrik Tijmen Verkouw, both of Sittingbourne, all of (GB)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/231,694

(22) Filed: Jan. 14, 1999

Related U.S. Application Data

(62) Division of application No. 08/694,071, filed on Aug. 8, 1996, now Pat. No. 5,900,466.

(30) Foreign Application Priority Data

Sep. 8, 1995 (EP) .................................................. 95306301

(51) Int. Cl.$^7$ ....................................................... C08F 8/14

(52) U.S. Cl. ......................... 525/384; 252/235; 525/327.7
(58) Field of Search .............................. 525/384; 252/235

(56) References Cited

U.S. PATENT DOCUMENTS

| 3,381,022 | 4/1968 | Le Guer . |
| 5,118,432 | 6/1992 | Emert et al. . |

FOREIGN PATENT DOCUMENTS

| 317354 | 11/1988 | (EP) . |
| 981850 | 10/1963 | (GB) . |
| 1483729 | 9/1973 | (GB) . |

*Primary Examiner*—Bernard Lipman

(57) ABSTRACT

Polyolefin-substituted dicarboxylic ester derivatives, having an ester group derived from a polyether polyol and process for making such; wherein the ester derivatives are useful additives in lubricating oil compositions and concentrates thereof.

6 Claims, No Drawings

1

POLYOLEFIN-SUBSTITUTED DICARBOXYLIC DERIVATIVES

This is a division of application Ser. No. 08/694,071 filed Aug. 8, 1996, now U.S. Pat. No. 5,920,466, the entire disclosure of which is hereby incorporated by reference.

FIELD OF THE INVENTION

The present invention relates to polyolefin-substituted dicarboxylic acid ester derivatives and polyolefin substituted dicarboxylic anhydride ester derivatives which are useful as dispersant additives in lubricating oil compositions.

BACKGROUND OF THE INVENTION

UK patent No. 981,850 discloses as oil additives esters of polyisobutenylsuccinic acids which are obtained by reaction of polyisobutenylsuccinic acids with a polyol, e.g. pentaerythritol. These products have are known dispersant additives for lubricating oils, and are often referred to as "ashless" because of the absence of a metal component.

It has now been found that by using a particular class of polyols it is possible to prepare polyolefin-substituted dicarboxylic acid or anhydride ester derivatives having improved dispersancy properties when compared with the conventional ester derivatives described hereinabove.

SUMMARY OF THE INVENTION

Accordingly, the present invention, there is provided polyolefin-substituted dicarboxylic acid ester derivatives and polyolefin substituted dicarboxylic anhydride ester derivative having (a) a polyolefin substituent derived from an atactic propylene oligomer of the formula:

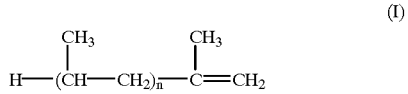

(I)

where n is in the range of 15 to 120, having a number average molecular weight (Mn) in the range of 700 to 5000 and molar ratio of dicarboxylic acid or dicarboxylic anhydride moieties to atactic propylene oligomer in the range of 1:1 to 1.5:1; and having (b) an ester group derived from a polyether polyol.

DESCRIPTION OF THE INVENTION

The polyether polyols may be prepared by the established reaction of one or more alkylene oxides e.g. ethylene oxide, propylene oxide, styrene oxide or epichlorohydrin with an alkane polyol for instance an alkylene diol or polyalkylene polyol.

The alkane polyols comprise at least two and preferably at least four hydroxy groups such as the trihydroxyalkanes, which includes, without limitations, ethylene glycol, propylene glycol, polymethylene glycols, trihydroxybutanes, pentanes, hexanes, heptanes, octanes, nonanes, dodecanes, which includes, without limitations, as well as tetrahydroxy alkanes, pentahydroxy alkanes, hexahydroxy alkanes, and the sugar alcohol's such as erythritol, pentaerythritol, tetritols, pentitols, hexitols, mannitol, sorbitol, sucrose, glucose and the like. Preferred polyols comprises sorbitol and glycerol or a mixture thereof. Especially preferred is sorbitol. The polyether polyols in accordance with the present invention may comprise one or more aromatic groups.

The alkylene diols or polyalkylene polyols may suitably be mixed with an amine, prior to their reaction with one or more alkylene oxides.

Suitable amines comprise amino-alcohol's, polyoxyalkylene polyamines and hydroxyamines. Preferably, the amine is an amino-alcohol.

The polyolefin-substituted dicarboxylic acid or anhydride ester derivative is suitably prepared by reacting a polyolefin-substituted dicarboxylic acid or anhydride with a polyether polyol as described hereinbefore. It will be clear that a polyether polyol comprises at least two alkoxy groups and at least two hydroxy groups.

The polyolefin-substituted dicarboxylic acid is preferably derived by reacting an alpha-beta unsaturated dicarboxylic acid with a polyolefin, suitably a homopolymer or copolymer of one or more olefin monomers having 2 to 16, preferably from 2 to 6, carbon atoms. The copolymers include random, block and tapered copolymers. Suitable monomers include ethene, propene, butenes, isobutene, pentenes, octenes, and also diolefins such as butadiene and isoprene. If a diene is used as monomer the resulting polymer is preferably hydrogenated to saturate at least 90%, more preferably substantially all unsaturated bonds. It is especially preferred to use polyolefin substituents derived from polyisobutylene or (atactic) polypropylene.

The polyolefin substituent may derive from any polyisobutylene.

Suitable polyisobutylene substituents include those disclosed in for instance UK 981,850, UK 2,081,274, UK 2,231,873 and EP-A-0 208 560 which are hereby fully incorporated by reference.

The polyolefin substituent may derive from any atactic propylene oligomer. Suitably, the polyolefin substituent is derived from the atactic polypropylene as described and claimed in EP-B-0 490 454 which document is hereby fully incorporated by reference.

The alkenyl-substituted dicarboxylic acid or anhydride ester derivative has a polyolefin substituent derived from an atactic propylene oligomer substantially of the formula

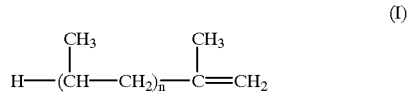

(I)

where n is in the range of 15 to 120, having number average molecular weight ($M_n$) in the range of 700 to 5000, and molar ratio of dicarboxylic acid or dicarboxylic anhydride moieties to atactic propylene oligomer in the range of 1:1 to 1.5:1. The number average molecular weight ($M_n$) of the polyolefin substituent is suitably not greater than 5000, since molecular weights above 5000 can give handling problems in the reaction due to the viscosity levels. To reduce the risk of problems the number average molecuilar weight is preferably below 3000 but above 700 since low molecular products tend to be less effective as dispersants. More preferably, $M_n$ is in the range 900 to 2500.

The number average molecular weight can easily be determined by vapour pressure osmometry or by gel permeation chromatography with calibration of the polymer, as will be appreciated by those skilled in the art.

The weight average molecular weight ($M_w$) can also be determined by gel permeation chromatography. The quotient $M_w/M_n$, which is a measure indicating the width of molecular weight distribution, has a value from 1.5 to 4.0.

The dicarboxylic acid is suitably derived from an alpha-beta unsaturated dicarboxylic acid, anhydride or ester, such as maleic, fumaric, itaconic, water maleic acid and anhydride being particularly preferred, in which case the dicarboxylic acid grouping in the present product is thus a succinic acid derivative.

Preferably, the polyolefin-succinic type derivatives in accordance with the present invention have a molar equivalent ratio of succinic groups to polyolefin groups of below 1.3. Such derivatives show particularly useful properties, including a reduced level of interaction with other additives normally present in lubricating oil packages, and moreover give good results in the more severe engine test VE. Preferably, the molar equivalent ratio of dicarboxylic acid producing groups to polyolefin groups is between 1.0 and 1.2.

It should be understood that for the purposes of the present invention the "molar equivalent ratio" is the molar ratio in the actual product of dicarboxylic acid or anhydride groupings to equivalents of polyolefin substituent. The molar equivalent ratio (r) can be easily calculated by the following expression:

$$r = \frac{M_n \times AV}{(20 \times AM - AV \times 96)}$$

in which:

$M_n$=Number average molecular weight of the polyolefin

AV=Acid value of the reaction product (mmol/g)

AM=Active matter in the reaction product (% m)

"Active matter" denotes polyolefins bearing carboxylic acid groupings, from which it will be understood that the unreacted nonpolar polyolefins do not contribute to the AM.

The molar ratio of dicarboxylic acid or anhydride groups to polyether polyol groups in the derivatives of the present invention is suitably in the range of 0.5 to 10, preferably in the range of 0.6 to 3, more preferably 0.8 to 2.2.

In accordance with the present invention, the polyolefin-substituted dicarboxylic or anhydride derivatives of the invention may be prepared by a process which comprises reacting a polyolefin-substituted dicarboxylic or anhydride as defined hereinabove with a polyether polyol.

The molar ratio of polyolefin-substituted dicarboxylic acid or anhydride to polyether polyol used in the present process may vary between wide limits. Suitably, the molar ratio of polyolefin-substituted dicarboxylic acid or anhydride to polyether polyol is in the range of 0.5 to 10, preferably 0.6 to 3. The reaction temperature may also vary between wide limits with reaction temperatures in the range 150° C. to 250° C. being suitable and in the range 180° C. to 210° C. being preferred. The reaction time may also vary between wide limits with reaction times in the range 6 to 30 hours being suitable and in the range 18 to 24 hours being preferred. A solvent may be present in the reaction mixture. Suitable examples of solvents include hydrocarbons, without limitations, such as xylene, toluene and mineral oil; ethers, such as, diphenylether; ketones; and chlorobenzene.

An esterfication catalyst may also be added. Conventional esterfication catalysts may be used. Suitable esterification catalysts include mineral acids, sulphonic acids and $BF_3$, mineral acids being preferred.

Water vapour which is produced during the reaction can be removed from the reaction zone as the reaction proceeds, by application of methods well known in the art. Suitably, the reaction is carried out in a closed reaction vessel.

The polyolefin-substituted dicarboxylic acid or anhydrides may be prepared according to established procedures from an alkene of required molecular weight and an appropriate amount of the dicarboxylic acid or anhydride. Thus, the polyolefin may be contacted with for instance maleic acid or anhydride at a temperature of 140 to 220° C., optionally in the presence of chlorine, for example as described in e.g. UK Patent 949,981, which is incorporated herein by reference. The proportions of polyolefin and maleic anhydride and also chlorine, when used, are selected so as to yield the desired MALA/polyolefin ratio in the final product. Another method for the preparation of polyolefin-substituted succinic anhydride is described in U.S. Pat. No. 3,172,892 which is incorporated herein by reference, according to which a halogenated, in particular chlorinated, polyolefin is reacted with maleic anhydride.

From NL-A-74 12 057 it is known to prepare hydrocarbon-substituted succinic anhydride by thermally reacting a polyolefin with maleic anhydride, a procedure which may be combined with that described in UK 949,981, as is illustrated in UK 1,440,219 and UK 1,543,627.which are incorporated herein by reference. The products prepared in this way include compounds in which the polyolefin chain is connected to the alpha and/or beta carbon atoms of the succinic group.

The polyolefin-substituted dicarboxylic acid or anhydride derivatives of the present invention find their prime application as additives for lubricating oil compositions, although they may be incorporated in hydrocarbon fuels such as gasolines.

Accordingly, the present invention further provides a lubricating oil composition which comprises a major proportion of the ester derivative(s) (more than 50% w) and a lubricating oil and a minor proportion of the ester derivative (s), preferably from 0.1 to 10% w, especially 0.5 to 5% w, based on the total composition of a derivative as defined hereinabove.

The lubricating oil used in such compositions can be natural, mineral or synthetic in origin. Natural lubricating oils include animal and vegetable oils, such as castor oil. Mineral oils comprise the lubricating oil fractions derived from crude oils, coal or shale, which fractions may have been subjected to certain treatments such as clay-acid, solvent or hydrogenation treatments. Synthetic lubricating oils include synthetic polymers of hydrocarbons, modified alkylene oxide polymers, and ester lubricants, which are known in the art. These lubricating oils are preferably crankcase lubricating oils for spark-ignition and compression-ignition engines, but include also hydraulic lubricants, metal-working fluids and automatic transmission fluids. The lubricating oil composition in accordance with the present invention may contain various other additives, known in the art, such as viscosity index improvers, e.g. linear or star-shaped polymers of a diene such as isoprene or butadiene, or a copolymer of such a diene with optionally substituted styrene. These copolymers are suitably block copolymers and are preferably hydrogenated to such an extent as to saturate most of the olefinic unsaturation. Other suitable additives include dispersant V.I. improvers such as those based on block copolymers, or polymethacrylates, extreme pressure/anti-wear additives such as zinc or sodium dithiophosphates, anti-oxidants, friction modifiers or metal-containing detergents such as phenates, sulphonates, alkyl-salicylates or naphthenates, all of which detergents may be overbased.

The lubricating oil composition according to the present invention has excellent dispersancy properties.

The lubricating oil composition according to the present invention is suitably prepared by blending an additives concentrate into the lubricating base oil. Such concentrate generally comprises a lubricating oil as solvent/diluent and one or more additives in a concentrated form. Hence, the present invention further provides a lubricating oil concentrate comprising a lubricating oil and a polyolefin-substituted dicarboxylic acid or anhydride derivative as decribed hereinabove, in an amount of 10 to 80% weight (w) based on the total concentrate.

The invention will now be illustrated by means of the following Examples which are included for illustrative purposes only and are not to be construed as limiting the invention.

EXAMPLE 1

An atactic propylene oligomer (APO) (Mn 1125) was prepared by a method analogous to that disclosed in Examples 1 to 4 of EP-B-0490454. The atactic propylene oligomer (700 g, 0.62 mol) and maleic anhydride (MALA) (183 g, 1.86 mol) were heated heated together at reflux temperature (200° C.) in a glass reactor equiped with baffles, turbine stirrer, reflux condenser, nitrogen inlet, temperature probe and electrical heating mantle for 24 hours. Unreacted MALA was removed by vacuum distillation. The residue was then allowed to cool to ambient temperature (20° C.), diluted with heptane to about 50% w and insoluble matter was removed by filtration. The heptane was then evaporated off yielding a clear, light yellow viscous liquid product (710 g) which was found to have active matter content of 95.4% w and acid value 1.89 milli-equivalents/g (meq/g). This analysis data indicates a succination ratio of 1.23 mol MALA/mol propylene oligomer.

Active matter content was determined by separating inactive material from the desired active matter on an aluminium oxide column using diethyl ether as eluant (AMS 807). Acid value was determined by potentiometric titration with aqueous potassium hydroxide of a weight amount of product dissolved in a toluene/methyl ethyl ketone/t-butanol/water mixture (SMS 2746). Results are given in Table 1.

EXAMPLE 2

A mixture of 2.5 kg (2.66 mol) polyisobutylene (PIB) (Mn 950) and 391 g (3.99 mol) of maleic anhydride (MALA), yielding a molar ratio of maleic anhydride to polyisobutylene of 1.5:1, was heated to 235° C. over 4 hours. The excess maleic anhydride was removed by evaporation under reduced pressure yielding a product which was found to have active matter content of 67.8% w and acid value 1.52 milli-equivalents/g (meq/g). This analysis data indicates a succination ratio of 1.20 mol MALA/mol polyisobutylene. Results are given in Table 1.

EXAMPLE 3

An atactic propylene oligomer (APO) (Mn 835) was prepared as described in Example 1. The atactic propylene oligomer obtained (21.37 g, 25.2 mol) and maleic anhydride (MALA) (4.63 kg, 47.2 mol) were heated together at reflux temperature (225° C.) in a glass reactor equiped with baffles, turbine stirrer, reflux condenser, nitrogen inlet, temperature probe and electrical heating mantle for 4 hours. Unreacted MALA was removed by vacuum distillation. The residue was then allowed to cool to ambient temperature (20° C.), diluted with heptane to about 50% w and insoluble matter was removed by filtration. The heptane was then evaporated off yielding a clear, light yellow viscous liquid product (25 kg) which was found to have active matter content of 77.9% w and acid value 1.87 milli-equivalents/g (meq/g). This analysis data indicates a succination ratio of 1.14 mol MALA/mol propylene oligomer.

EXAMPLE 4

A mixture of 250 g (0.112 mol) polyisobutylene (PIB) (Mn 2640) and 27.5 g (0.28 mol) of maleic anhydride (MALA), yielding a molar ratio of maleic anhydride to polyisobutylene of 2.5:1, was heated to 225° C. over 8 hours. The excess maleic anhydride was removed by evaporation under reduced pressure yielding a product which was found to have active matter content of 63.2% w and acid value 0.567 milli-equivalents/g (meq/g). This analysis data indicates a succination ratio of 1.24 mol MALA/mol polyisobutylene. Results are given in Table 1.

EXAMPLE 5

The APO-MALA product (150 g (0.14 mol) obtained in Example 1 was then heated to 130° C. in a similar glass reactor as mentioned above, after which a propoxylated Sorbitol/glycerol mixture (weight ratio 54:46) (70.5 g, 0.17 mol) was added in portions over time. The resultant reaction mixture was then heated at 200° C. for 20 hours. The water formed during the reaction was removed by a Dean and Stark apparatus. The product so obtained was a clear dispersant which was found to have active matter content of 95.6% w and acid value 0.09 milli-equivalents/g (meq/g). This analysis data indicates an esterification ratio of 1:1.21 mol APO-MALA/mol propoxylated Sorbitol/glycerol. Results are given in Table 1.

EXAMPLE 6

The PIB-MALA product (1 kg, 0.6 mol) obtained in Example 2 was subjected to a similar process as described in Example 5, except that 258 g (0.63 mol) of the propoxylated Sorbitol/glycerol mixture was used. The product obtained was a clear dispersant which was found to have active matter content of 65.1% w and acid value 0.13 milli-equivalents/g (meq/g). This analysis data indicates an esterfication ratio of 1:1.05 mol PIB-MALA/mol propoxylated Sorbitol/glycerol. Results are given in Table 1.

EXAMPLE 7

The PIB-MALA product (1000 g, 0.597 mol) obtained in Example 2 was subjected to a similar process as described in Example 5, except that 282 g (0.451 mol) propoxylated Sorbitol was used instead of the propoxylated Sorbitol/glycerol mixture. The product obtained was a clear dispersant which was found to have active matter content of 63.0% w and acid value 0.11 milli-equivalents/g (meq/g). This analysis data indicates an esterification ratio of 1:0.755 mol PIB-MALA/mol Sorbitol. Results are given in Table 1.

EXAMPLE 8

The PIB-MALA product (1200 g, 0.293 mol) obtained in Example 4 was subjected to a similar process as described in Example 5, except that 159 g (0.254 mol) propoxylated Sorbitol was used instead of the propoxylated Sorbitol/glycerol mixture. The product obtained was a clear dispersant which was found to have active matter content of 62.6% w and acid value 0.05 milli-equivalents-/g (meq/g). This analysis data indicates an esterification ratio of 1:0.868 mol PIB-MALA/mol Sorbitol. Results are given in Table 1.

EXAMPLE 9 (COMPARATIVE)

The APO-MALA product (51.55 g, 0.62 mol) obtained in Example 3, HVI 60 oil (47 g) and pentaerythritol (PENTA) (10.94 g, 0.08 mol) were heated in an autoclave at 200° C. for 12 hours. The product so obtained was a clear dispersant which was found to have active matter content of 50.0% w and acid value 0.08 milli-equivalents/g (meq/g). This analysis data indicates an esterification ratio of 1:1.3 mol APO-MALA/mol PENTA. Results are given in Table 1.

EXAMPLE 10 (COMPARATIVE)

The PIB-MALA product (121.0 g, 0.066 mol) obtained in Example 2 and pentaerylthritol (11.75 g, 0.086 mol) were subjected to a similar process as described in Example 9. The product obtained was a clear dispersant which was found to have active matter content of 67.2% w and acid value 0.08 milli-equivalents/g (meq/g). This analysis data indicates an esterfication ratio of 1:1.3 mol PIB-MALA/mol PENTA. Results are given in Table 1.

EXAMPLE 11 (COMPARATIVE)

The APO-MALA product (100 g, 0.094 mol) obtained in Example 3 and 0.5% w p-toluene sulphonic acid were subjected to a similar process as described in Example 5, except that Cellosolve (16.8 g, 0.187 mol) was used instead of the propoxylated Sorbitol/glycerol mixture, and a temperature was applied of 160° C. for 16 hours. The product obtained was a clear dispersant which was found to have active matter content of 79.5% w and acid value 0.11 milli-equivalents/g (meq/g). This analysis data indicates an esterfication ratio of 1:2 mol PIB-MALA/mol Cellosolve. Results are given in Table 1.

EXAMPLE 12 (COMPARATIVE)

The PIB-MALA product (100 g, 0.055 mol) obtained in Example 2 and 0.5% w p-toluenesulphonic acid were subjected to a similar process as described in Example 5, except that Cellosolve (9.9 g, 0.11 mol), was used instead of the propoxylated Sorbitol/glycerol mixture, and a temperature was applied of 160° C. for 18 hours. The product obtained was a clear dispersant which was found to have active matter content of 66.7% w and acid value 0.08 milli-equivalents/g (meq/g). This analysis data indicates an esterfication ratio of 1:2 mol PIB-MALA/mol Cellosolve. Results are given in Table 1.

EXAMPLE 13 (COMPARATIVE)

The APO-MALA product (100 g, 0.094 mol) obtained in Example 3 and 0.5% w p-toluenesulphonic acid were subjected to a similar process as described in Example 5, except that Carbitol (25.1 g, 0.187 mol) was used instead of the propoxylated Sorbitol/glycerol mixture, and a temperature was applied of 160° C. for 16 hours. The product obtained was a clear dispersant which was found to have active matter content of 81.3% w and acid value 0.14 milli-equivalents/g (meq/g). This analysis data indicates an esterfication ratio of 1:2 mol PIB-MALA/mol Carbitol. Results are given in Table 1.

EXAMPLE 14 (COMPARATIVE)

The PIB-MALA product (100 g, 0.055 mol) obtained in Example 2 and 0.5% w p-toluenesulphonic acid were subjected to a similar process as described in Example 5, except that Carbitol (14.7 g, 0.11 mol) was used instead of the propoxylated Sorbitol/glycerol mixture, and a temperature was applied of 200° C. for 18 hours. The product obtained was a clear dispersant which was found to have active matter content of 68.3% w and acid value 0.15 milli-equivalents/g (meq/g). This analysis data indicates an esterfication ratio of 1:2 mol PIB-MALA/mol Carbitol. Results are given in Table 1.

EXAMPLE 15 (COMPARATIVE)

The PIB-MALA product (100 g, 0.022 mol) obtained in Example 4 and 0.5% w p-toluenesulphonic acid were subjected to a similar process as described in Example 5, except that Cellosolve (3.9 g, 0.044 mol) was used instead of the propoxylated Sorbitol/glycerol mixture, and a temperature was applied of 180° C. for 18 hours. The product obtained was a clear dispersant which was found to have active matter content of 66.2% w and acid value 0.12 milli-equivalents/g (meq/g). This analysis data indicates an esterfication ratio of 1:2 mol PIB-MALA/mol Cellosolve. Results are given in Table 1.

EXAMPLE 16 (COMPARATIVE)

The PIB-MALA product (100 g, 0.022 mol) obtained in Example 4 and 0.5% w p-toluenesulphonic acid were subjected to a similar process as described in Example 5, except that Carbitol (5.8 g, 0.044 mol) was used instead of the propoxylated Sorbitol/glycerol mixture, and a temperature was applied of 200° C. for 18 hours. The product obtained was a clear dispersant which was found to have active matter content of 66.9% w and acid value 0.08 milli-equivalents/g (meq/g). This analysis data indicates an esterfication ratio of 1:2 mol PIB-MALA/mol Carbitol. Results are given in Table 1.

EXAMPLE 17

The products of Examples 5 to 16 were each diluted to an active matter content of 50% w by addition of "HVI 60"1 base oil (a bright and clear high viscosity index base oil having viscosity at 100° C. 4.4 to 4.9 $mm^2/s$ (ASTM D 2270)). The resulting concentrates were then tested as follows:

Carbon Black Dispersancy Test (CBDT) (British Rail publication BR 669 : 1984)

Samples of a SAE 15W40 Middle East lubricating oil containing a commercial package of a zinc dialkyldithiophosphate, an overbased calcium alkyl salicylate and VI improver, were modified by incorporation of concentrate to give oils containing the products of Examples 5 to 16 at a concentration of 1% w active matter. 3% w of carbon black was then added to each oil and (percentage) increase in kinematic viscosity at 60° C. was determined using an Ubbelohde viscometer. A low result is an indication for less sludge forming in engines and indicates therefore good dispersancy performance.

The results are shown in Table 2. It will be clear from Table 2 that the composition according to the present invention (Examples 5 to 8) performs much more attractively than compositions falling just outside the scope of the present invention (Examples 9 to 16).

TABLE 1

| Product of Ex. | Active matter (% w) | Acid value (meg/g) | Succin./ester. Ratio |
| --- | --- | --- | --- |
| 1 | 95.4 | 1.89 | 1.23 |
| 2 | 67.8 | 1.52 | 1.20 |
| 3 | 77.9 | 1.82 | 1.14 |
| 4 | 63.2 | 0.567 | 1.24 |
| 5 | 95.6 | 0.09 | 1.21 |
| 6 | 65.1 | 0.13 | 1.05 |
| 7 | 63.0 | 0.11 | 0.755 |
| 8 | 62.6 | 0.05 | 0.868 |
| 9 | 50.0 | 0.08 | 1.3 |
| 10 | 67.2 | 0.08 | 1.3 |
| 11 | 79.5 | 0.11 | 2.0 |
| 12 | 66.7 | 0.08 | 2.0 |
| 13 | 81.3 | 0.14 | 2.0 |

TABLE 1-continued

| Product of Ex. | Active matter (% w) | Acid value (meg/g) | Succin./ester. Ratio |
|---|---|---|---|
| 14 | 68.3 | 0.15 | 2.0 |
| 15 | 66.2 | 0.12 | 2.0 |
| 16 | 66.9 | 0.08 | 2.0 |

TABLE 2

| Product of Example | CBDT (%) |
|---|---|
| 5 | 22.8 |
| 6 | 24.5 |
| 7 | 23.6 |
| 8 | 23.8 |
| 9 | 32.0 |
| 10 | 37.0 |
| 11 | 47.2 |
| 12 | 60.3 |
| 13 | 50.0 |
| 14 | 58.4 |
| 15 | 54.7 |
| 16 | 46.9 |

What is claimed is:

1. A process for the preparation of a polyolefin-substituted dicarboxylic acid or anhydride ester derivative which comprises reacting a polyolefin-substituted dicarboxylic acid or anhydride with a polyether polyol substantially free of non-ether functional groups; wherein said polyether polyol is prepared from reaction of at least one alkylene oxide and an alkane polyol having at least four hydroxy groups.

2. The process of claim 1, wherein a temperature is applied in the range of 150° C. to 250° C.

3. The process of claim 1, wherein the molar ratio polyolefin-substituted dicarboxylic acid to polyether polyol is in the range of 0.5 to 10.

4. A lubricating oil composition which comprises a major proportion of a lubricating oil and a minor proportion of a polyolefin-substituted dicarboxylic acid or anhydride ester derivative having an ester group derived from a polyether polyol substantially free of non-ether functional groups; wherein said polyether polyol is prepared from reaction of at least one alkylene oxide and an alkane polyol having at least four hydroxy groups.

5. The lubricating oil composition of claim 4, which contains from 0.1 to 10% w, based on the total composition, of the ester derivative.

6. A lubricating oil concentrate which comprises a lubricating oil and 10 to 80% w, based on the total concentrate, of a polyolefin-substituted dicarboxylic acid or anhydride ester derivative having an ester group derived from a polyether polyol substantially free of non-ether functional groups; wherein said polyether polyol is prepared from reaction of at least one alkylene oxide and an alkane polyol having at least four hydroxy groups.

* * * * *